US00PP37422P2

(12) United States Plant Patent
Hansen

(10) Patent No.: US PP37,422 P2
(45) Date of Patent: May 12, 2026

(54) ***HEMEROCALLIS* PLANT NAMED 'Bright Note'**

(50) Latin Name: ***Hemerocallis* (L.) hybrid**
Varietal Denomination: Bright Note

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,947

(22) Filed: Dec. 2, 2025

(51) Int. Cl.
*A01H 5/02* (2018.01)
*A01H 6/00* (2018.01)

(52) U.S. Cl.
USPC ..... Plt./312

(58) Field of Classification Search
USPC ..... Plt./312
See application file for complete search history.

*Primary Examiner* — Susan Mccormick Ewoldt

(57) ABSTRACT

A new and distinct *Hemerocallis* plant named 'Bright Note' characterized by winter-hardy compact habit with clean medium-green foliage that goes dormant in the winter. The flowers are fragrant, single, nocturnal, rounded, with overlapping sunny yellow tepals and a green throat. Flowering begins about mid-July with excellent coverage and reliable repeating until hard frost.

2 Drawing Sheets

Botanical classification: *Hemerocallis* (L.) hybrid.
Variety denomination: 'Bright Note'.

STATEMENT REGARDING PRIOR DISCLOSURES UNDER 37 CFR 1.77(B)(6)

The first of sale was made to Down to Earth Garden Center by Walters Gardens, Inc. on Jan. 21, 2025. On Feb. 1, 2025, a photograph and brief description of the new plant were also uploaded on a website of Walters Gardens, Inc. and on Jun. 3, 2025, the new plant was advertised in the "Walters Gardens 2025-2026 Catalog". Walters Gardens, Inc. obtained the new plant and all information relating thereto from the inventor. The cultivar was registered in 2025 with the American Daylily Society which is the International Cultivar Registration Authority for the genus *Hemerocallis* with a brief description and photograph. No plants of *Hemerocallis* 'Bright Note' have been sold in this country or anywhere in the world, nor has any disclosure of the new plant been made more than one year prior to the filing date of this application and such sale or disclosure within one year was either derived directly or indirectly from the inventor.

BACKGROUND AND ORIGIN OF THE PLANT

The present invention relates to a new and distinct daylily plant, *Hemerocallis* 'Bright Note' hereinafter also referred to as the new plant or just the cultivar name 'Bright Note'. *Hemerocallis* 'Bright Note' was hybridized by the inventor on Jun. 26, 2013, in a trial garden at a wholesale perennial nursery in Zeeland, Michigan, USA. The female or seed parent was 'Busting Out All Over' (not patented) and the male or pollen parent was 'Bitsy' (not patented).

The new plant was selected as a single seedling from this cross, and after initial confidential evaluations in a trial bed beginning in 2015 at the same nursery was assigned the breeder code 13-7-2 through the remaining trials. The new plant has been asexually propagated by division at the same wholesale nursery in Zeeland, MI since 2015 with all resultant asexually propagated plants having retained all the same unique traits as the original plant in successive generations of asexual reproduction.

There are over 110,000 registered daylilies with The American *Hemerocallis* Society, which is the International Cultivar Registration Authority for the genus *Hemerocallis*. In comparison to the new plant, the female parent has a taller habit with fewer flowers per scape of pale cream-yellow with a green throat. The male parent has a shorter habit with smaller flowers of lemon yellow with a green throat on shorter scapes with fewer flowers per scape.

The most similar daylily cultivars known to the inventor are 'Beach Blonde' (not patented), 'Early Cecilia' (not patented), 'Going Bananas' U.S. Plant Pat. No. 17,164, 'Happy Returns' (not patented), 'Quint Quandary' (not patented) and 'Stella de Oro' (not patented). 'Beach Blonde' has taller flower stems and larger flowers with tepals that vary in color from platinum blonde to light yellow, and the tepas are narrower and less flat. 'Early Cecilia' has taller flower scapes with slightly larger flowers that are solid light yellow without a green throat. 'Going Bananas' has a slightly larger habit, larger flowers, lighter yellow tepals that are lightly creped and more undulate, and a green throat. 'Happy Returns' has flowers of a similar size and scape height, but the tepals have more finely-ruffled margins, and the flower lacks the green throat. 'Quint Quandary' has very light yellow flowers with fewer flowers per scape. 'Stella de Oro' has a much short scape with fewer flowers that are slightly smaller and a deeper gold color.

*Hemerocallis* 'Bright Note' differs from all other daylilies known to the applicant, by the combination of the following traits:

1. Winter-hardy, compact habit with clean medium-green foliage that goes dormant in the winter;
2. Fragrant, single, nocturnal, rounded flowers about 7 cm across of sunny yellow tepals with a green throat;
3. Inner and outer tepals imbricate tepals on either side;

4. Plants produce scapes to about 52 cm tall with up to 15 flowers per scape;
5. Flowering begins about mid-July with excellent coverage with excellent repeat flowering late in the season until hard frost.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
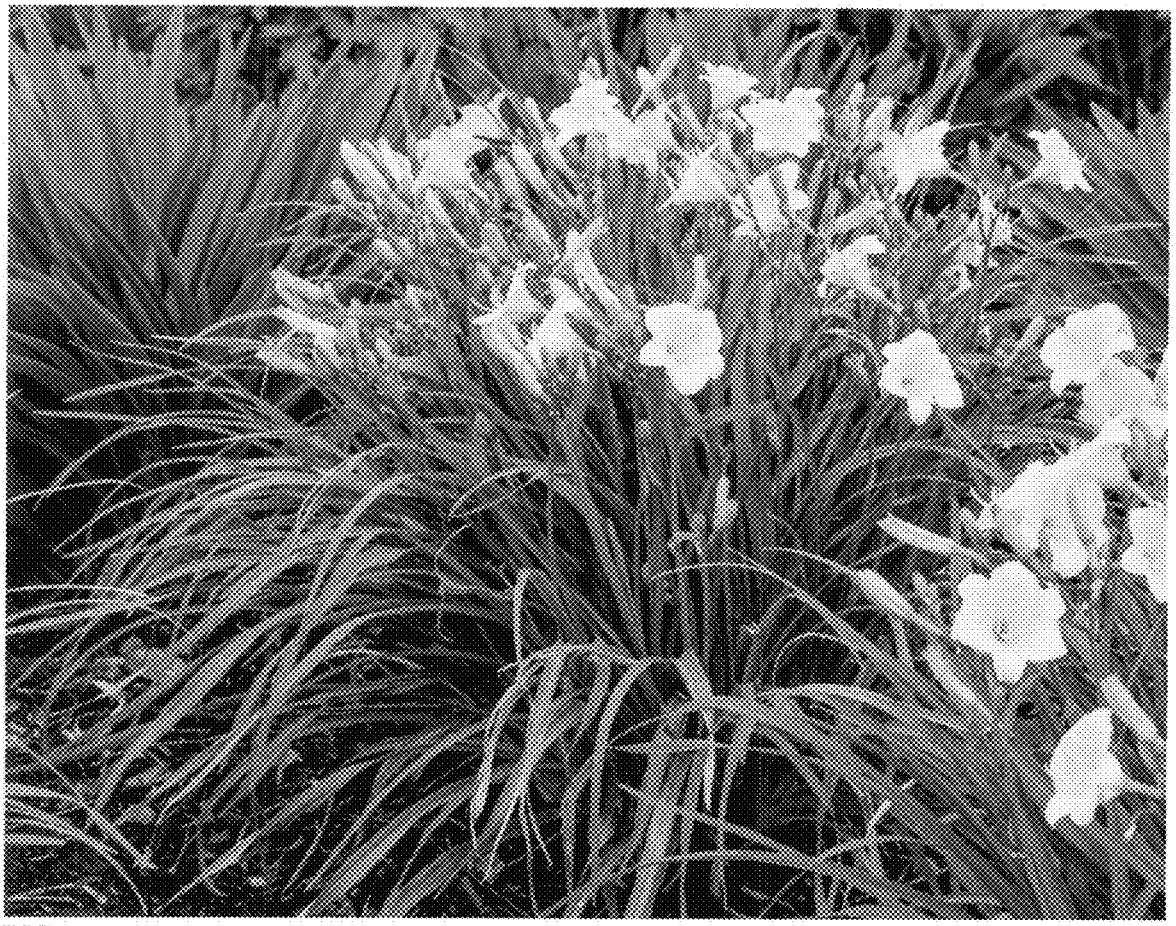
FIG. 1 shows a five-year-old plant in peak flower in a sunny trial landscape during mid-summer in Zeeland, Michigan.
Figure 2:
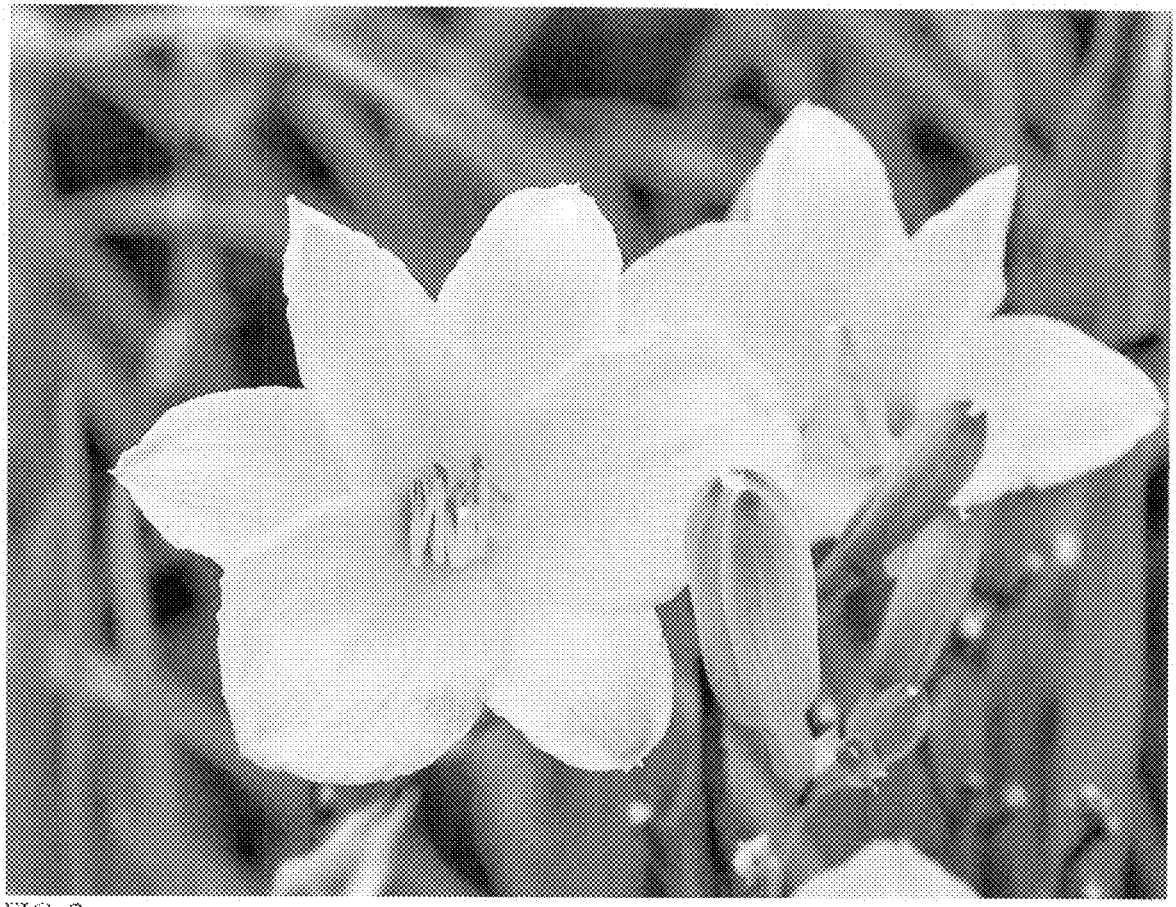
FIG. 2 shows a close-up of the flowers with buds.

The following descriptions and color references are based on the 2015 edition of The Royal Horticultural Society Colour Chart except where common dictionary terms are used. The new plant, *Hemerocallis* 'Bright Note', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Michigan with and supplemental water and fertilizer.

Botanical classification: *Hemerocallis* (L.) hybrid;

Parentage: Female (seed) parent is 'Busting Out All Over'; male (pollen) is 'Bitsy';

Propagation: Division of the rhizome;

Growth rate: Moderate to rapid;

Crop time: about 8 to 10 weeks to flower starting in spring in a 3.8-liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with four basal shoots emerging from rhizomes producing a radially symmetrical mound of arching leaves;

Plant size: Foliage height about 38 cm tall from soil line to the top of the leaves, about 60 cm wide at the widest point; flowering to about 52 cm tall;

Leaves: Linear; apex narrowly acute; base sheathing, sessile; entire; glabrous, slightly glaucous abaxial and adaxial; folded; to about 33.5 cm long and 14 mm across, average about 31 cm long and about 10 mm across; about 14 leaves per division;

Cauline leaves: 1 per scape about one-third of the way up the peduncle to flowers; reduced, about 3 to 7 cm long and 9 mm across;

Leaf color: Cauline and basal young abaxial between RHS 137C and RHS 137D, adaxial between RHS 137C and RHS 137B; mature adaxial between RHS 146B and RHS 138A, mature abaxial nearest RHS 146B; mature cauline and basal leaves adaxial nearest RHS 146A, abaxial nearest RHS 137B;

Veins: Parallel; color adaxial nearest RHS 146A and abaxial nearest RHS 137B;

Flower description:

Flowers: Funnelform; single, with two sets of three tepals; zygomorphic, incomplete; up to 28 per scape, mostly distally arranged on typically 4 branches; aspect upward and outwardly; about 7 cm across and 7 cm tall to exserted stigma, corolla about 5 cm deep; corolla tube diameter at fusion about 7 mm, length from base to fusion point about 2.5 cm long; nocturnal; individually lasting for about one day; peduncle remains effective from mid-June into early-September for approximately six weeks in Zeeland, Michigan with repeating until hard frost;

Inflorescence: Upwardly, erect; to about 22 cm tall and flowering to about 15 cm across; with two branches and about 11 flowers;

Flower fragrance: None detected;

Buds about one day prior to opening: Oblate ellipsoid with bluntly acute apex and tepals beginning to separate, and basal one-fifth narrowed terete; about 5.5 cm long and about 1.1 cm in diameter at widest point with basal 1.7 cm narrowing to about 0.5 cm diameter;

Bud color one day from opening: Apex nearest RHS 146B, main inflated bulb portion between RHS 7A and RHS 153D, base of inflated bulb portion nearest RHS 146C, basal 17 mm between RHS N144A and N144D;

Tepals: 2 sets of 3;

Inner tepals: Ovate; glabrous; rounded apex; base truncate, fused in proximal 2.5 cm; with slight undulation on the margin; midrib fluted about 2 mm wide on abaxial and costate on adaxial surface; recurved nearly 90 degrees in distal one-fifth; width at fusion about 5 mm, about 3.1 cm across at widest point and about 7 cm long;

Outer tepals: Ovate; glabrous; rounded to apiculate apex; base truncate, fused in proximal 2.5 cm; flat; midrib not obvious; tepals reflexed about 90 degrees in distal one-fifth; fused in proximal 2.5 cm; width at fusion about 5 mm, about 1.8 cm across at widest point and 7 cm long;

Inner tepal color: Adaxial nearest RHS 5A with the basal throat nearest RHS N144B; abaxial nearest RHS 9A in the distal two-thirds and in the proximal one-third nearest RHS N144A;

Outer tepal color: Adaxial nearest RHS 6A with the basal throat nearest RHS N144B; abaxial nearest RHS 9A in the distal two-thirds and in the proximal one-third nearest RHS N144A;

Pedicel: Cylindrical; slightly glaucous; from 2 to 5 mm long and 2 mm diameter; subtended by bract;

Pedicel color: Nearest RHS 137C;

Bract: Ovate; with acute apex and truncate base; to 15 mm long and 9 mm across, decreasing distally;

Bract color: Adaxial and abaxial distal center nearest RHS 144A, proximally hyaline and between RHS 160D and RHS 11D;

Peduncle: Cylindrical; glabrous; slightly glaucous; about 16 per plant during peak initial flowering, repeating, producing a second set after the first set is done flowering, erect to about 20 cm tall and 5 mm diameter at base, average about 18 cm tall; extending above foliage;

Peduncle color: Between RHS 144A and RHS 138B;

Gynoecium: Single; tri-carpelled; glabrous; about 71 mm long;

*Style*.—Single; cylindrical; about 64 mm long, 1 mm diameter, arcuate slightly upward at distal one-third; color distally nearest RHS 16A, middle nearest RHS 4C, and proximally nearest RHS 2D.

*Stigma*.—Globose; 1 mm diameter; color nearest RHS 7A.

*Ovary*.—Conical; smooth; acute apex, truncate base; about 6 mm long and 2 mm diameter at base; color nearest RHS 143B.

Androecium: Six; glabrous;

*Filaments*.—Six; cylindrical distally, slightly applanate proximally; adnate to inner tepal in basal 21 mm above ovary; arcuate upward in distal 10 mm; free in distal 33 mm long from fusion point on tepal; to about 53 mm long, 2 mm across near tepal attachment, and 1 mm thick; color where fused with adaxial corolla nearest RHS N144D, distally nearest RHS 6A, center nearest RHS 16A, and proximally above fusion nearest RHS 1B.

*Anthers*.—Oblong; dorsifixed, longitudinal; about 6 mm long and 2 mm wide; color between RHS 200C and RHS N199A.

*Pollen*.—Less than 0.1 mm long; color nearest RHS 17A.

Fruit: Abundant under natural pollination; tri-loculicidal dehiscent capsule; loosely three-sided ellipsoidal; rounded apex and base; to about 3 cm long and 1.7 cm wide near middle; color when maturing base nearest RHS 145D and apex nearest RHS 146A; when mature at dehiscence nearest RHS 161B;

Seeds: Oblong ellipse to irregular globose; non-fleshy, dried berry; about 6 to 15 per capsule; nearly-round dried berry; about 6 mm long and 4 mm across; color nearest RHS 202A;

Disease and pest resistance and tolerance: 'Bright Note' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage and light shade during the hottest period of the day, but is able to tolerate some drought when mature and direct sun without leaf burn when. provided sufficient water.

Hardiness at least from USDA zone 3 through 9, and other disease resistance and tolerance is typical of that of other daylilies. The new plant is useful for landscaping en masse, as a single specimen or small groups.

I claim:

1. A new and distinct ornamental daylily plant named *Hemerocallis* 'Bright Note' as herein described and illustrated.

* * * * *